United States Patent [19]
Devine et al.

[11] Patent Number: 6,027,904
[45] Date of Patent: Feb. 22, 2000

[54] PLATELET COUNT ASSAY USING THROMBOSPONDIN OR β-THROMBOGLOBULIN

[75] Inventors: Dana Virginia Devine; Donald Elliott Brooks, both of Vancouver, Canada

[73] Assignee: University of British Columbia, Canada

[21] Appl. No.: 08/947,981

[22] Filed: Oct. 9, 1997

Related U.S. Application Data

[63] Continuation-in-part of application No. 08/625,770, Mar. 29, 1996, abandoned, and a continuation-in-part of application No. PCT/US97/05081, Mar. 27, 1997.

[51] Int. Cl.$^7$ .................. G01N 33/53; G01N 33/536; G01N 33/543
[52] U.S. Cl. .................. 435/7.21; 422/57; 435/7.9; 435/7.92; 435/7.93; 435/7.94; 435/13; 435/287.2; 435/287.9; 435/970; 436/514; 436/524; 436/528; 436/531; 436/534; 436/536; 436/87; 436/169
[58] Field of Search .................. 435/7.2, 7.21, 435/7.9, 7.92, 7.93, 7.94, 13, 970, 287.2, 287.3, 287.7, 287.8, 287.9, 288.6, 288.7; 436/514, 524, 528, 531, 533, 534, 548, 69, 87, 164, 169, 170, 172, 174, 807, 536; 422/56, 57

[56] References Cited

U.S. PATENT DOCUMENTS

| | | | |
|---|---|---|---|
| 3,884,579 | 5/1975 | Mauthner | 356/39 |
| 4,610,960 | 9/1986 | Mosher | 436/548 |
| 5,238,652 | 8/1993 | Sun et al. | 422/58 |
| 5,256,538 | 10/1993 | Aiken et al. | 435/7.9 |
| 5,356,782 | 10/1994 | Moorman et al. | 435/7.92 |
| 5,384,264 | 1/1995 | Chen et al. | 422/514 |
| 5,648,274 | 7/1997 | Chandler et al. | 436/514 |
| 5,753,517 | 5/1998 | Brooks et al. | 436/514 |

FOREIGN PATENT DOCUMENTS

| | | |
|---|---|---|
| 0417818A1 | 3/1991 | European Pat. Off. |
| 58-11753 | 7/1983 | Japan |
| 88/08534 | 11/1988 | WIPO |
| 97/37229 | 10/1997 | WIPO |

OTHER PUBLICATIONS

Michelson et al., 1996. In vivo tracking of platelets: circulating degranualted platelets rapidly lose surface P–selectin but continue to circulate and function. Proc. Natl. Acad. Sci. USA 93: 11877–82, 1996.

Zeller et al., 1999. Circulating platelets show increased activation in patients with acute cerebral ischemia. Thromb. Haemost. 81:373–7.

Dawes et al., 1978. The release, distribution, and clearance of human beta–thromboglobulin and platelet factor 4. Thrombosis Res. 12: 851–61.

Majumdar et al., Mar. 1991. Characterization of the human beta–thromboglobulin gene: comparison with the gene for platelet factor 4. Journal of Biolog. Chem. 266: 5785–9.

George, J.N., Sep. 1990. Platelet immunoglobin G: its significance for the evaluation of thrombocytopenia and for understanding the origin of alpha–granule proteins. Blood 76:859–70.

Kelton et al., 1985. Comparison of the measurement of surface or total platelet–associated IgG in the diagnosis of immune thrombocytopenia. Am. J. Hematol. 18: 1–5.

Kelton et al., 1983. The amount of platelet–bound albumin parallels the amount of IgG on washed platelets from patients with immune thrombocytopenia. Blood 62: 924–7.

Takahashi, et al., "Measurement of platelet factor 4 and β–thromboglobulin by an enzyme–linked immunosorbent assay," (from *Chem. Abstracts*, 1998, 109(13), Abstract No. 107305Z).

Zhang, Q. et al., "Application of ELISA in clinical determination of plasma β–thromboglobulin (βTG) and platelet factor 4 (PF$_4$) in clinics," *Zhonghua Xeuyexue Zazhi* 11(4):172–174 (1990). (from *Chem. Abstracts*, 1990, 113 (21), Abstract No. 187508p.

Pumphrey et al., 1983 Platelet alpha granule depletion: findings in patients with prosthetic heart valves and following cardiopulmonary bypasssurgery. Thrombosis Res. 30:257–264.

Niewiarowski et al., 1976. Immunoassay of human platelt factor 4 (PF4, antiheparin factor) by radial immunodiffusion. J. Lab. Clin. Med. 87:720–733.

Kao et al., 1986. A monoclonal anitbody–based enzyme–linked immunosorbent assay for quantitation of plasma thrombospondin Am. J. Clin. Pathol. 86:317–323.

Takahashi et al., 1988. Measurement of platelet factor 4 and β–thromboglobulin by an enzyme–linked immunosorbent assay Clin. Chim. Acta. 175:113–114.

Abrams et al., 1991. Immunological detection of activated platelets in clinical disorders. Thrombosis and Haemostasis 65:467–473.

*Primary Examiner*—Christopher L. Chin
*Assistant Examiner*—James L. Grun
*Attorney, Agent, or Firm*—Hamilton, Brook, Smith & Reynolds, P.C.

[57] ABSTRACT

Methods of calculating the platelet count of an individual, by measuring the amount of a released platelet granule protein of interest in a sample of whole blood or of platelet-rich plasma from the individual, are described. The platelet granule protein of interest is either thrombospondin or β-thromboglobulin. The amount of released platelet granule protein of interest in the whole blood sample or platelet-rich plasma sample is measured using an enzyme-linked immunosorbent assay; radioimmunoassay; sandwich assay; a quantitative immunochromatographic assay; or non-solid phase nephelometry. The platelet count is directly related to the amount of released platelet granule protein of interest in the sample, and can be determined from the amount of platelet granule protein of interest that is released from a known number of platelets.

8 Claims, 7 Drawing Sheets

PLATELET COUNT ASSAY USING THROMBOSPONDIN OR β-THROMBOGLOBULIN

RELATED APPLICATIONS

This application is a Continuation-in-Part application of U.S. Ser. No. 08/625,770, filed Mar. 29, 1996, now abandoned, and of the U.S. designation in international application PCT/US97/05081, filed Mar. 27, 1997. The entire teachings of these applications are incorporated herein by reference.

BACKGROUND OF THE INVENTION

In a wide variety of clinical and therapeutic situations, blood platelet counts are routinely needed. Abnormalities in platelet counts can cause significant bleeding problems in a patient, and may indicate a multitude of underlying conditions. Measurement of blood platelet counts typically requires complex instrumentation and a clinical laboratory. Automated hematology analyzers can be used to obtain platelet counts over a wide range of values; however, manual hemacytometer counts are necessary for measurement of low platelet counts. Other blood constituents, such as red and white blood cells, as well as instrument artifacts may interfere with accurate assessment of platelet count. Methods for determination of platelet count by a simple, portable procedure are necessary.

SUMMARY OF THE INVENTION

The invention relates to methods of determining the platelet count of an individual, by measuring the amount of a platelet granule protein of interest that is released from platelets in a blood sample from the individual, or the amount of a platelet granule protein of interest that is released from platelets in a platelet-rich plasma sample derived from the blood sample from the individual. The platelet granule proteins of interest are thrombospondin and β-thromboglobulin. The amount of a platelet granule protein of interest is measured using an appropriate quantitative means, such as an enzyme-linked immunosorbent assay; a quantitative immunochromatographic assay; or other appropriate means. The platelet count of the individual is determined from the amount of the platelet granule protein of interest; the determination is based on a relationship between the amount of released platelet granule protein of interest and platelet count. The relationship is a quantitative positive correlation between the platelet count in a sample of blood (or platelet-rich plasma) and the amount of the platelet granule protein of interest that is released from platelets upon clotting.

The methods of the invention provide swift, accurate determination of platelet count, including low platelet counts, without complex instrumentation. Furthermore, the methods provide an on-site method for platelet count determination at the point of care of the patient, and do not require skilled technical labor to perform.

The methods of the invention are particularly useful for individuals who have been treated with heparin. Heparin is frequently used as an intravenous drug during surgery, and is also used to rinse indwelling catheters in order to prevent clotting. Individuals who have been treated intravenously with heparin frequently develop antibodies to complexes of heparin and platelet factor 4, another platelet granule protein (see, for example, Visentin, G. P. et al., *J. Clin. Investigation* 93(1):81–8 (1994)). The development of antibodies to the complex of heparin and platelet factor 4 may contribute to the onset of potentially life-threatening conditions, such as heparin-induced thrombocytopenia (HIT) and heparin-associated thrombocytopenia with thrombosis (HATT). An accurate measurement of platelet count is critical to the diagnosis and treatment of HIT and HATT. A determination of platelet count based on platelet factor 4 would not be accurate, due to interference of the antibodies in the measurement of platelet factor 4. Thrombospondin or β-thromboglobulin can be used in a determination of platelet count, without concern about antibodies in the test sample that would interfere with an accurate measurement. This is particularly important for patients who may have been exposed to heparin unknowingly, such as by heparin flush of an intravenous catheter.

DETAILED DESCRIPTION OF THE INVENTION

The current invention pertains to methods of determining platelet count. As described herein, Applicants have discovered a relationship between the amount of thrombospondin, or the amount of β-thromboglobulin, released from platelets in a sample and the platelet count. The platelet count in a sample of blood (or platelet-rich plasma) directly correlates with the amount of thrombospondin and the amount of β-thromboglobulin released from platelets upon clotting. The correlation is constant from individual to individual, and is not dependent on disease state.

As a result of this discovery, methods are now available to determine the platelet count of an individual by measuring the amount of a released platelet granule protein of interest in a sample of whole blood or of platelet-rich plasma. The term, "platelet granule protein," as used herein, refers to a protein or peptide that is released from platelet granules during clotting. A "platelet granule protein of interest", as used herein, is either thrombospondin or β-thromboglobulin. Platelet factor 4, another platelet granule protein, is not included within the platelet granule proteins of interest, because individuals treated with heparin, for whom measurement of platelet count is frequently performed, may have antibodies to a complex of heparin and platelet factor 4. Such antibodies would interfere with accurate measurement of platelet factor 4 and thereby render inaccurate a determination of platelet count based on platelet factor 4. Platelet factor 4 is also excluded from the platelet granule proteins of interest, because of the association between antibodies to the complex of heparin and platelet factor and conditions such as heparin-induced thrombocytopenia (HIT) and heparin-associated thrombocytopenia with thrombosis (HATT). Thus, the platelet granule proteins of interest are also referred to herein as "non-thrombocytopenia-associated platelet granule proteins".

A sample of blood is obtained from the individual for whom the platelet count will be determined, using standard methods. Approximately 100–500 μl of blood are typically drawn; the amount of blood that is used will vary, depending on the method used to quantify the platelet granule protein. If platelet-rich plasma is used to determine the platelet count, a platelet-rich plasma sample is isolated from the blood sample, using standard methods.

Platelet granule proteins are released from platelets in the whole blood sample or in the platelet-rich plasma sample, using methods such as a releasing agent, or contact activation. Releasing agents such as thrombin, calcium ionophore A23187, phorbol esters and detergents, can all be used to release platelet granule proteins from platelets. More than one releasing agent can also be used. Alternatively, thrombin generation by the natural clotting process that is initiated by contact activation when blood is drawn into glass containers in the absence of anticoagulant is sufficient for the purposes of the invention. Thus, addition of an agent to release the platelet granule proteins is not necessary if blood is allowed to clot naturally by contact activation. The platelet granule proteins released by the releasing agent or by contact activation are referred to herein as "released platelet granule proteins." A sample of whole blood, or a platelet-rich plasma sample, that contains released platelet granule proteins, is referred to herein as a "test sample".

After release of platelet granule proteins from the platelets, the amount of a platelet granule protein of interest in the test sample is measured. The platelet granule protein of interest (also referred to as the "released platelet granule protein of interest") is either thrombospondin or β-thromboglobulin. Both platelet granule proteins of interest can be measured. Any method which quantitatively measures the platelet granule protein of interest can be used. Appropriate methods include, but are not limited to, enzyme-linked immunosorbent assay (ELISA); radioimmunoassay; sandwich assay; non-solid phase nephelometry; and quantitative immunochromatographic assay (Kemeny, D. M. and Challacombe, S. J. (eds), ELISA and Other Solid Phase Immunoassays: Theoretical and Practical Aspects, John Wiley and Sons, New York (1988)).

In a preferred embodiment of the invention, released platelet granule protein of interest is measured using an enzyme-linked immunosorbent assay (ELISA). The ELISA can be performed as an inhibition ELISA (Kemeny, D. M. and Challacombe, S. J. (eds), ELISA and Other Solid Phase Immunoassays: Theoretical and Practical Aspects, John Wiley and Sons, New York (1988)), in which the platelet granule protein of interest that is present in a test sample binds to anti-(platelet granule protein) antibody, making the antibody unavailable to bind to a platelet granule protein-coated microtitre well. A microtitre plate coated with the platelet granule protein of interest is used. An appropriate anti-(platelet granule protein of interest) antibody is incubated with a test sample for an appropriate length of time to allow binding of the anti-(platelet granule protein of interest) antibody to the platelet granule protein, if present, in the test samples. The test sample-antibody mixture is exposed to the microtitre plate coated with the platelet granule protein of interest for an appropriate length of time to allow antibody in the test sample-antibody mixture to bind to the platelet granule protein of interest that is immobilized on the plate. Unbound protein is washed from the microtitre plate wells with an appropriate buffer, such as Tris-buffered saline, and the bound anti-(platelet granule protein of interest) antibody is detected by an appropriate means, such as by incubating with an alkaline phosphatase-conjugated anti-(anti-platelet granule protein of interest antibody) IgG. A chromogenic substrate, such as p-nitrophenyl phosphate, is used to detect the signal of the bound antibody. Alternatively, other appropriate labels for the IgG antibodies can be used, such as peroxidase-conjugated anti-IgG; radiolabels; colloidal gold label; or fluorescent label. A detection means that is appropriate for the label is used. For example, an optical signal can be determined using an ELISA plate reader.

The amount of the platelet granule protein of interest in the sample is determined based on a standard curve. The standard curve for the platelet granule protein of interest is generated by preparing a series of control samples of known concentrations of the platelet granule protein of interest in serum or platelet-poor plasma containing no detectable platelet granule protein of interest. Anti-(platelet granule protein of interest) antibody is incubated with the test samples; the ELISA is performed on the series of control samples at the same time as the test sample, on the same platelet granule protein of interest-coated microtitre plate, and the values are plotted as a function of the concentration of platelet granule protein of interest included in the control samples.

After the amount of released platelet granule protein of interest in the test sample is measured, the platelet count can be determined. The determination is based on the amount of platelet granule protein of interest that is released from a known number of platelets. To determine platelet count, a reference curve (also herein referred to as the "granule protein/platelet curve") can be established by plotting the amount of platelet granule protein of interest in control samples against platelet counts determined by a standard hematology counter. Control samples (such as whole blood or platelet-rich plasma samples) include samples from normal donors and samples from donors with abnormally low platelet counts. At least approximately 20 normal donors and 10 donors with abnormally low platelet counts should be used for generation of the granule protein/platelet reference curve. The curve should contain samples from donors with platelet counts at or below $10 \times 10^9$/L in order to determine the shape of the line for the full range of anticipated platelet counts. The amount of platelet granule protein of interest is plotted against the platelet count. The platelet count from a test sample is determined by referring to the granule protein/platelet curve.

Alternatively, the reference curve can be generated using serum from blood containing a known number of platelets. ELISA values for the platelet granule protein of interest can then be plotted as a function of the platelet number, and the platelet count for a test sample can be determined directly from the ELISA results for the test sample.

In another embodiment of the invention, released platelet granule protein of interest is measured using a quantitative immunochromatographic assay. In one example of a quantitative immunochromatographic assay, the assay utilizes a rapid antigen measurement platform (RAMP™) apparatus. The apparatus includes a membrane strip made of a suitable material, such as cellulose nitrate or glass fiber, which has sufficient porosity and the ability to be wet by the fluid containing the analyte, and which allows movement of particles by capillary action. The membrane strip has an application point, a contact region, and a detection zone; the contact region is between the application point and the detection zone. Imbedded in the contact region is a population of particles, such as colloidal metal particles, organic molecules, liposomes, or organic polymer latex particles. The particles are coated with an antibody to the platelet granule protein of interest. The particles can be labeled, using a calorimetric, fluorescent, luminescent, or other appropriate label, to facilitate detection. A detection reagent is immobilized in the detection zone. The detection reagent can be antibody to platelet granule protein, or can be the platelet granule protein itself. The apparatus can also include one or more of the following features: an application pad, which rests on and covers the application point; a contact pad, which rests on and covers the contact region, and which may have antibody-coated particles imbedded within it; if a contact pad is present, a separator pad, which rests on the membrane in between the contact region and the contact pad; a wicking pad, which rests on the membrane adjacent to the detection zone, on the opposite side of the detection zone from the contact region; and an internal control, which includes internal control particles imbedded in the contact region, a control detection reagent, and a control reaction zone.

In order to conduct the quantitative assay for platelet granule protein of interest using whole blood or a platelet-rich plasma sample, the platelet granule proteins must be released from the platelets, either before application of the sample to the apparatus, or by application of the sample to the apparatus. The platelet granule proteins can be released from platelets in the whole blood sample or in the platelet-rich plasma sample by the methods described above. In a preferred embodiment, the RAMP™ apparatus includes an application pad, which is used to release the platelet granule proteins from platelets. The whole blood sample or the platelet-rich plasma sample is applied to the application pad and release of the platelet granule proteins results. The application pad can additionally be impregnated with one or more releasing agent(s), such as those described above, to facilitate release of the platelet granule protein. The platelet granule proteins released by the releasing agent or by contact activation are referred to herein as "released platelet granule proteins."

To conduct the assay, the application point (or application pad) of the membrane strip is contacted with the fluid sample. The apparatus is then maintained under conditions which are sufficient to allow capillary action of fluid to transport released platelet granule proteins, if present in the sample, through the membrane strip to the contact region. The apparatus is further maintained under appropriate conditions so that when the platelet granule proteins reaches the contact region, platelet granule protein of interest binds to the antibody-coated particles imbedded in the contact region. Antibody-coated particles which have been maintained under conditions allowing platelet granule protein of interest in the fluid to bind to the antibody-coated particles imbedded in the contact region, and/or the contact pad, if present, are referred to herein as "contacted antibody-coated particles". Contacted antibody-coated particles may or may not have platelet granule protein of interest bound to the antibodies. Contacted antibody-coated particles, including those which are bound with platelet granule protein of interest, are mobilized by fluid and move by capillary action through the strip to the detection zone. The detection reagent interacts with platelet granule protein-bound antibody-coated particles, forming detection-reagent-particle complexes. The detection-reagent-particle-complexes are arrested (e.g., immobilized) in the detection zone. The amount of (platelet granule protein of interest)-bound antibody-coated particles that are arrested in the detection zone is then detected. The amount of platelet granule protein of interest in the fluid sample is related to the amount of (platelet granule protein of interest)-bound antibody-coated particles that are arrested in the detection zone: if the detection reagent is the platelet granule protein of interest, the amount of platelet granule protein of interest in the fluid sample is inversely related; if the detection reagent is antibody against the same epitope of the platelet granule protein of interest as those antibodies coated onto the particles, or antibody against a different epitope of the platelet granule protein of interest as those antibodies coated onto the particles, the amount of platelet granule protein of interest in the fluid sample is directly related. The amount of platelet granule protein of interest is determined from a standard curve.

In an alternative immunochromatographic assay, the fluid sample containing platelet granule protein of interest is applied directly to the detection zone of the apparatus. In this embodiment, the detection reagent is antibody to the platelet granule protein of interest. The apparatus is maintained under appropriate conditions so that platelet granule protein of interest in the fluid sample interacts with the detection reagent, and is immobilized in the detection zone. Water or an appropriate buffer is then added to the application point of the membrane to mobilize the antibody-coated particles, which are moved by capillary action into the detection zone. The apparatus is further maintained under conditions which allow interaction of the antibody-coated particles with platelet granule protein of interest that is immobilized in the detection zone. Interaction of the antibody-coated particles with immobilized platelet granule protein arrests movement of the antibody-coated particles. The amount of platelet granule protein of interest in the fluid sample is related to the amount of antibody-coated particles that are arrested in the detection zone, and is determined from a standard curve.

The standard curve for a platelet granule protein of interest is generated by preparing a series of control samples of known concentrations of the platelet granule protein of interest in serum or platelet-poor plasma containing no detectable platelet granule protein of interest. The quantitative immunochromatographic assay is performed on the series of control samples; the amount of detection-reagent-particles complexes in the detection zone is determined for each control sample; and the values are plotted as a function of the concentration of platelet granule protein of interest included in the control samples. Alternatively, blood samples having known numbers of platelets can be used as control samples, and the amount of platelet granule protein of interest can be plotted against platelet count, in a similar manner as described above for the ELISA.

More detailed teachings of quantitative immunochromatographic assays are described in U.S. patent application Ser. No. 08/625,048 (Attorney Docket Number UBC95-094), entitled "Quantitative Immunochromatographic Assays", filed on Mar. 29, 1996, the entire teachings of which are incorporated herein by reference.

The invention is now further illustrated by the following Examples, which are not intended to be limiting in any way.

EXAMPLE 1

Isolation of Thrombospondin for Development of ELISA Assay

Purified thrombospondin was isolated from fresh platelets obtained as platelet concentrates prepared from anticoagulated blood (Canadian Red Cross Society Blood Services, Vancouver Centre). Platelet concentrates can be prepared as described in the American Association of Blood Banks Technical Manual, 11th edition (Walker, R. H. (ed), Bethesda, Md., 1993). Thrombospondin was isolated using a modified protocol of the method described by Slayter (*Methods in Enzymology* 169:251–268 (1989)). Briefly, a single preparation started with four units of platelets which were diluted by 20% in acid citrate dextrose. After low speed centrifugation to remove contaminating red cells, the platelets were pelleted by centrifugation and resuspended in phosphate-buffered saline containing glucose, pH 6.5 (0.15 M NaCl, 4.3 mM $K_2HPO_4$, 4.3 mM $Na_2HPO_4$, 24 mM $NaH_2PO_4$ and 5 mM glucose). After two washes in this buffer, platelets were resuspended in 25 ml of Tris-saline with glucose, pH 7.5 (20 mM Tris-HCl, 0.15 M NaCl, 5 mM glucose) and pH was adjusted to 7.5, if necessary. The platelet suspension was warmed to 37° C. and 75 U of thrombin were added. After a two minute incubation, thrombin and any released platelet proteases were inhibited by the addition of 6 U/ml hirudin, 2 mM phenylmethylsulfonyl fluoride, 0.1 mg/ml leupeptin, 2 ug/ml aprotinin and 1 mM EDTA. The platelets were removed by centrifugation and the supernatant fluid concentrated 2–3 fold. This concentrated platelet releasate was applied to a Sepharose 4B gel filtration column (Pharmacia, Piscataway, N.J.) equilibrated in Tris-saline containing 1 mM EDTA. Thrombospondin positive fractions were pooled and purification assessed by SDS polyacrylamide gel electrophoresis (Laemmli, U. K. and M. Favre, *J. Mol. Biol.* 80:575 (1973)). Confirmation of the protein as thrombospondin was obtained by Western blotting (Towbin, H. et al., *Proc. Natl. Acad. Sci. USA* 76:4350 (1979)). Protein concentrations were determined by bichinchonic acid assay (Pierce Chemicals, Rockford, Ill.). If the preparation was not sufficiently pure, the material was passed through a heparin-Sepharose column (Pharmacia, Piscataway, N.J.) to remove impurities. In general, sufficient purity was achieved in the gel filtration step alone. The average yield of purified thrombospondin from 4 units of platelets is approximately 2–3 mg.

EXAMPLE 2

Development of ELISA Assay for Thrombospondin

Figure 1:
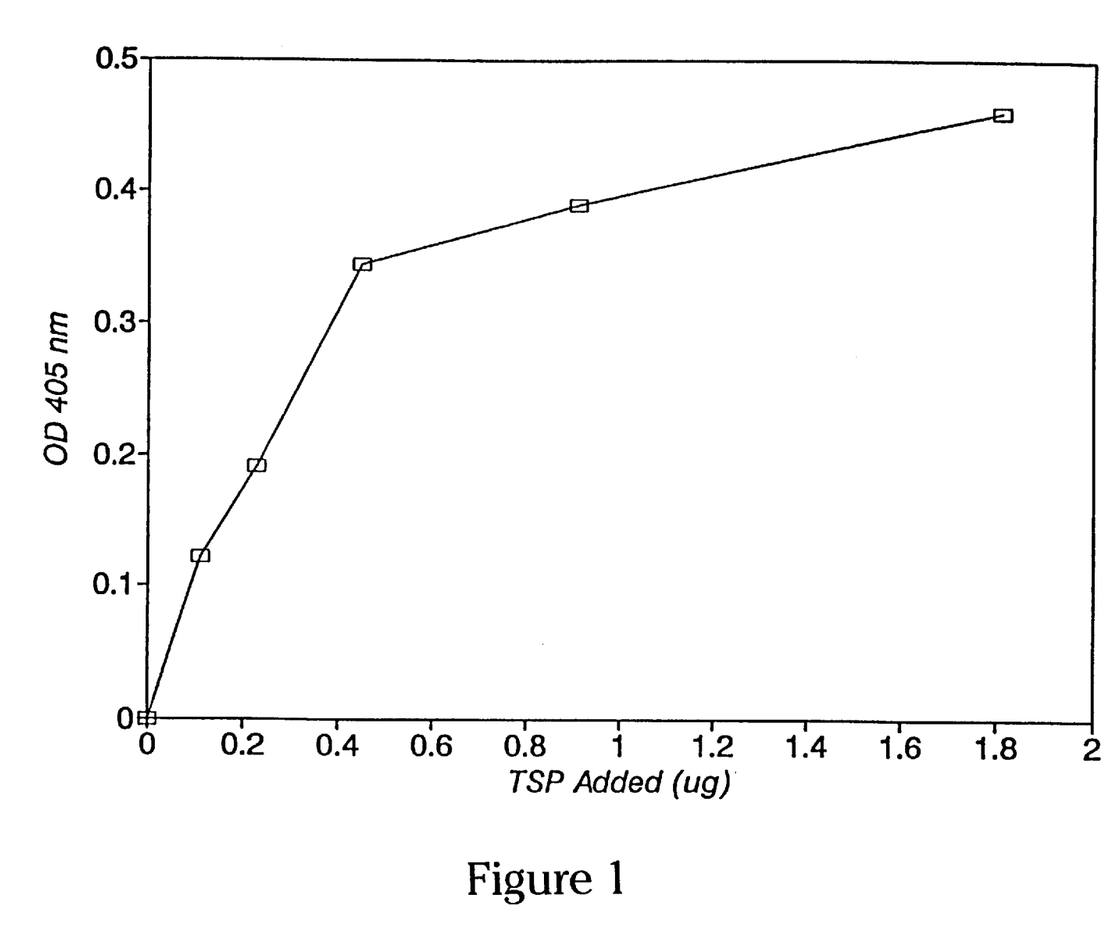
FIG. 1 is a graphic representation of a thrombospondin standard curve using a sandwich ELISA assay.

A direct capture, enzyme-linked immunosorbent assay (ELISA) was initially developed to assay column fractions for thrombospondin. A polyclonal ammonium sulphate fraction (approximately 80% IgG) of anti-thrombospondin antibody was used to coat ELISA plates and was sufficient to follow thrombospondin purification. When it was calibrated with the standard thrombospondin it was found to give inconsistent results, perhaps due to plate variation and age. Immulon 4 plates were ordered and the coating and blocking procedure standardized, as follows: 20 µg/ml Ab overnight at 4° C.; wash three times with blocking buffer consisting of Tris buffered saline (TBS) plus 3% BSA; then block with blocking buffer for one hour at room temperature. The coated plates were incubated with thrombospondin standards in buffer overnight at 4° C., washed to remove unbound protein, and then reacted with Sigma monoclonal Ab (1:1000) and developed with alkaline phosphatase-conjugated goat anti-mouse IgG (1:6,000; one hour at room temperature). A strong signal and a smooth, reproducible standard curve were obtained but the curve flattened at higher concentrations (FIG. 1).

Figure 2:
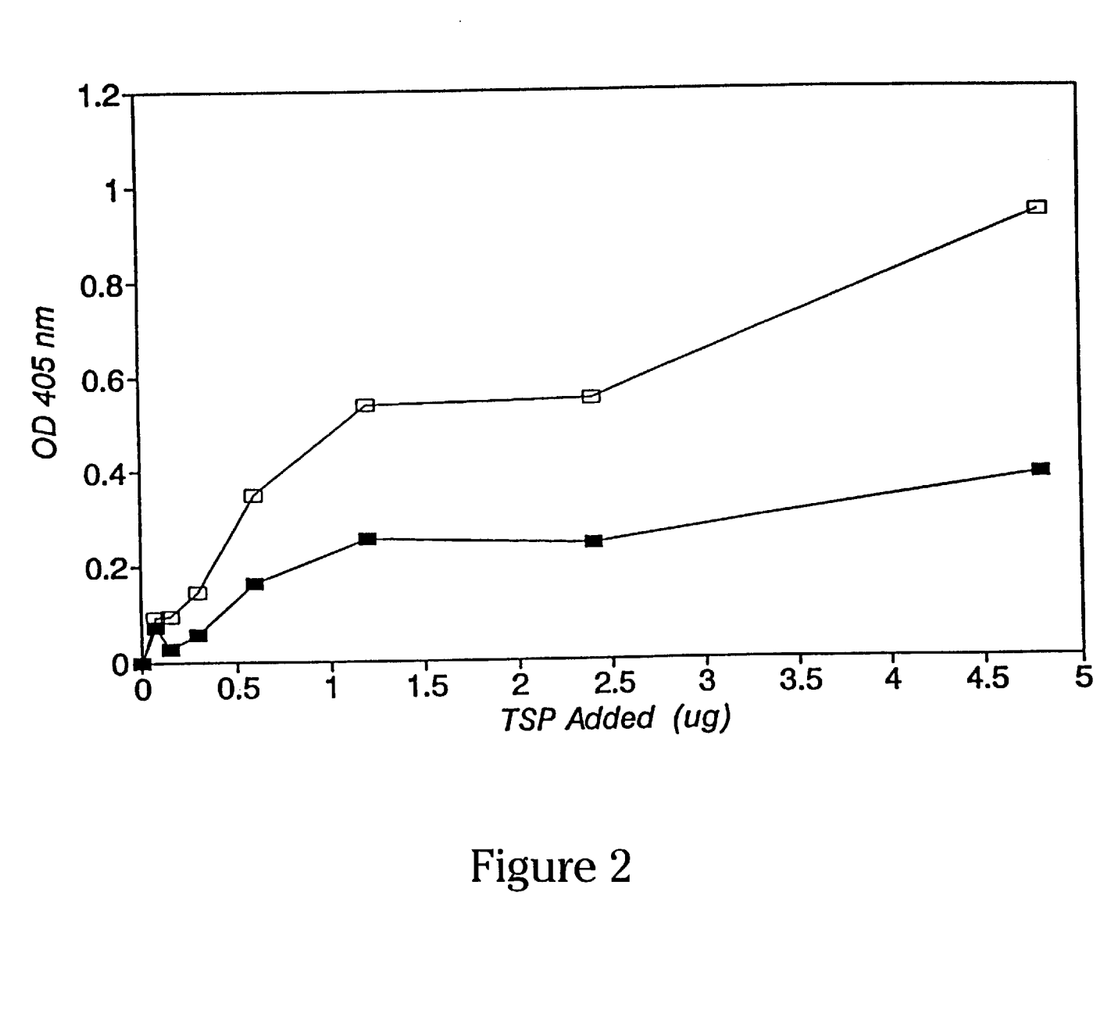
FIG. 2 is a graphic representation of the effect of blocking with thrombospondin-depleted plasma on the thrombospondin ELISA. Open squares, without plasma; filled squares, with plasma.

When serum dilutions were used in the above ELISA, a smooth dilution curve was obtained when the serum was diluted with buffer 1:1 or more; undiluted serum strongly reduced the signal. Because it was desirable to use the assay directly on whole clotted blood, a variety of experiments were designed to examine the problem of reduced signal with undiluted serum. It was found that, when a standard curve of thrombospondin was run in buffer, after the plates as coated were incubated overnight with thrombospondin-depleted serum (made by running serum through a heparin affinity column) and then washed, the signal was reduced by approximately 50% compared to a standard curve run on plates not incubated in serum. These results suggested that the serum was removing antibody from the plate by competitive adsorption (FIG. 2).

To solve this problem, a competitive inhibition ELISA assay was performed, which relied on the inhibition of anti-thrombospondin antibody binding to a thrombospondin-coated microtitre well by any thrombospondin present in a sample of serum from clotted blood, or any other blood sample in which the platelets have been stimulated to release their contents. Thrombospondin, rather than IgG, was adsorbed to the ELISA plates. Thrombospondin levels in solution were assayed by incubating the monoclonal antibody with the test solution before exposing the test solution to the plate. The concentration of thrombospondin in solution determined the number of monoclonal antibodies that were bound up by thrombospondin and thus unable to bind to thrombospondin on the plate. The ELISA signal was thereby reduced by an amount that is directly related to the thrombospondin concentration in the test solution. The advantage of this approach is that thrombospondin is a larger, "stickier" molecule than IgG and was expected to adsorb more strongly to the wells. This approach proved successful in reducing the problem of reduced signal when whole blood samples were used.

Figure 3:
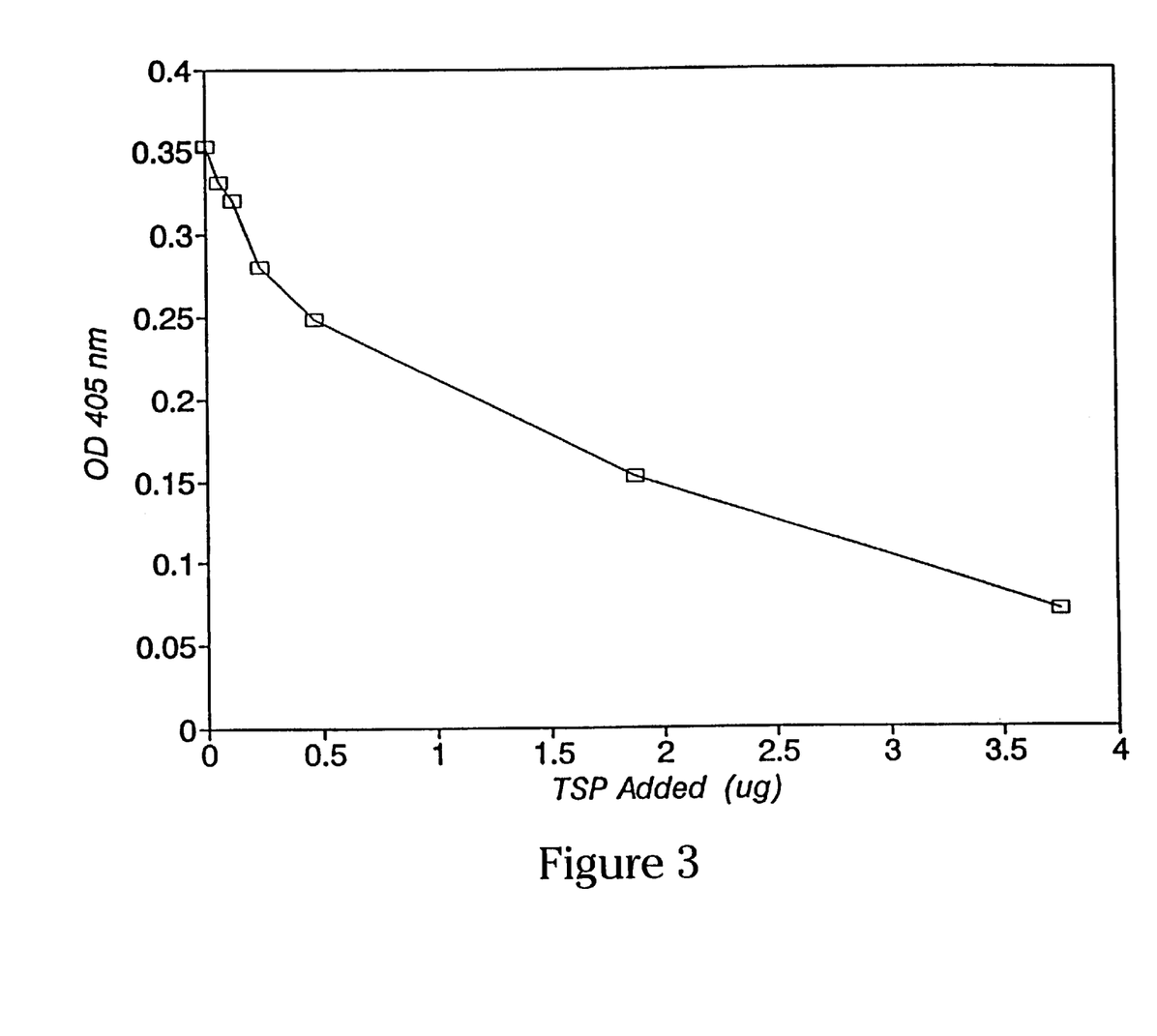
FIG. 3 is a graphic representation of the standard curve for platelet count, using a competitive thrombospondin inhibition ELISA.

To perform the competitive inhibition ELISA, plates were coated with 10 µg/ml of thrombospondin, isolated as described in Example 1. Plates were incubated overnight at 4° C., then washed and blocked by incubating in Tris-buffered saline containing 3% bovine serum albumin for one hour at room temperature. Test solutions were incubated with 1:1000 dilutions of ascites fluid containing monoclonal anti-thrombospondin antibody (Sigma Chemicals, St. Louis, Mo.) for 20 minutes at room temperature, then exposed to the coated plates for 45 minutes at room temperature, washed and developed. The resulting inhibition standard curve is shown in FIG. 3. This inhibition standard curve covers the entire range anticipated from clotted whole bloods. The inhibition assay performs similarly well in the presence of whole serum (data not shown).

The important factors identified in the development of the inhibition ELISA were the affinity of the monoclonal antibody, which influences the appropriate concentration in the test, and the anticipated amount of thrombospondin to be detected. Initially this assay was optimized using different concentrations of antibody, and different concentrations of thrombospondin in a matrix design. The concentration of antibody was chosen that gave a steep curve at concentrations of thrombospondin expected in samples with a platelet count within the normal range (150–300×10⁹/L). The assay was also set up at a lower concentration of antibody that would provide appropriate discrimination of platelet counts in thrombocytopenic samples (10–150×10⁹/L). These antibody binding studies predicted that the thrombospondin ELISA accurately estimates platelet count in either a clinically normal, or clinically abnormal, range.

EXAMPLE 3

Correlation Between Platelet Count and Thrombospondin Concentration

Figure 4:
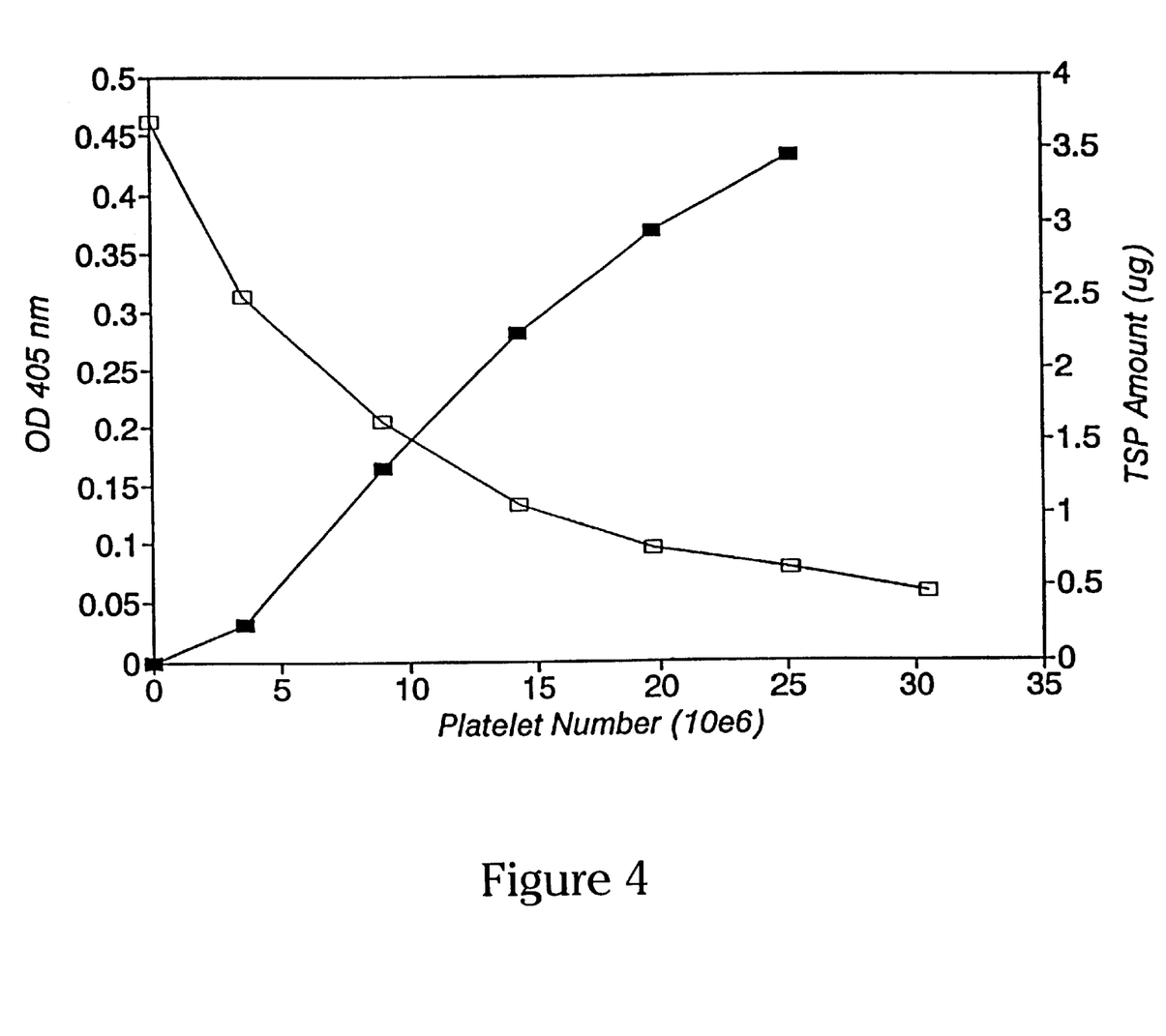
FIG. 4 is a graphic representation of OD and thrombospondin concentration interpreted from a standard curve plotted as a function of the platelet count. Closed squares, ug of thrombospondin; open squares, OD at 405 nm.

To demonstrate that the immunoassay for thrombospondin can be interpreted to give a measure of the platelet count in the donor's blood, experiments were done in which fresh citrated platelet-poor plasma was isolated and mixed in various proportions with citrated whole blood from a donor with a naturally high (but within normal range) platelet count, thus varying the platelet count in whole blood. Calcium (20 mM final concentration, added as 1 M $CaCl_2$) was then added to clot the blood and release thrombospondin into the serum. Serum was isolated by centrifugation and duplicate 100 µl samples incubated with 10 µl of 1:100 dilution of ascites fluid containing anti-thrombospondin antibodies (Sigma Chemicals, St. Louis, Mo.) fluid as above. The competitive inhibition ELISA was then performed. A tube of blood from the same donor was also taken into EDTA and submitted to the Hematology laboratory for routine platelet counting by the Model T660 or Model STCKR Coulter Counter (Coulter, Hialeah, Fla.). Utilizing a standard curve generated on the same plate with purified thrombospondin, the OD resulting from each platelet concentration, calculated from the whole blood count, was interpreted to give the thrombospondin concentration in serum. Both the OD and the thrombospondin concentration interpreted from the standard curve are plotted as a function of the platelet count determined by the Coulter Counter (FIG. 4). It is seen that a smooth curve is obtained, implying that the OD values can readily be interpreted in terms of platelet count with the use of the standard curve.

In order to examine the variation in the ability of the thrombospondin ELISA to measure platelet counts over a population, blood samples were drawn initially from five normal donors (the "initial study"). In each case samples were submitted for platelet counts by the Hematology Laboratory. One tube from each donor was allowed to clot naturally, with no additives, and each was subjected to the thrombospondin competitive ELISA described above. The results, shown in FIG. 5, indicated that agreement between the Counter and thrombospondin ELISA results in the initial study is quite good for all donors, demonstrating that the ELISA works well in whole serum. Hence, adsorption of TSP to polystyrene plates was not significantly reversed by exposure to serum for 45 minutes at room temperature.

A second, larger study was undertaken on a larger population of 26 normal donors. The last of the available isolated thrombospondin was used for the study, as there was insufficient commercial material available at that time. Enough purified thrombospondin was available to coat the plates according to the established protocol, but the amount was insufficient to run a standard curve on thrombospondin in buffer to determine the optimal concentration of antibody. This would have been desirable since a new batch of ascites fluid (Sigma Chemicals, St. Louis, Mo.) containing the anti-thrombospondin monoclonal antibody was used. It was assumed that this material would have the same concentration dependence as the antibody used to produce the results shown in FIG. 5. Hence, it was used at the recommended dilution.

Figure 5:
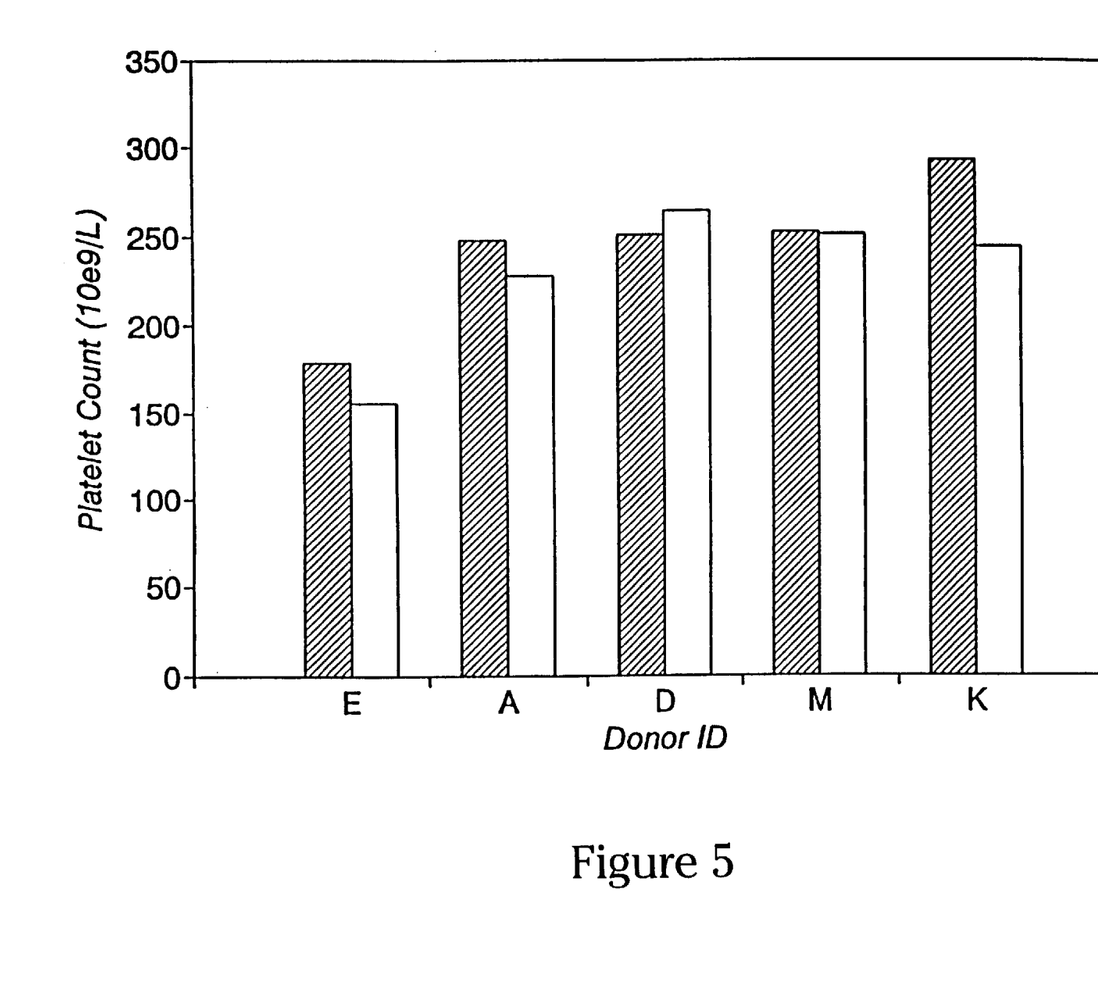
FIG. 5 is a graphic representation of the correlation between platelet counts obtained from Coulter counter and inhibition ELISA for six individuals in an initial study. Filled bars, Coulter counter; open bars, thrombospondin ELISA.
Figure 6:
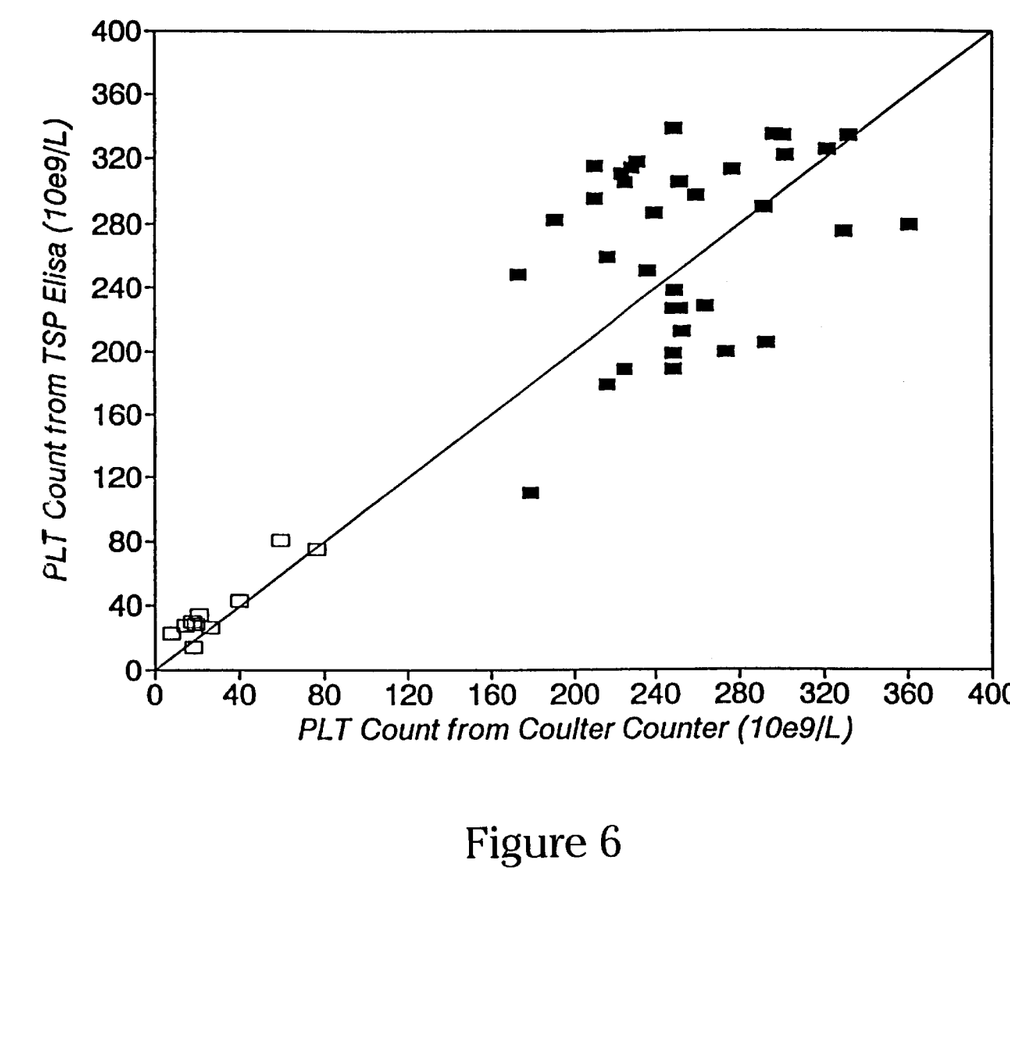
FIG. 6 is a graphic representation of a calibration curve demonstrating sensitivity of the thrombospondin inhibition ELISA over the normal range, on 32 samples from normal donors (closed squares) and 10 samples from donors with thrombocytopenia (open squares).

The same procedure as followed in generating FIG. 5 was used: the calibration curve to convert OD to platelet number was generated directly from measurements on a series of dilutions of citrated whole blood with citrated platelet-poor plasma, followed by re-calcification to initiate clotting and release the thrombospondin. The result is shown in FIG. 6. Closed squares represent normal donors. It is seen that the curve is of the expected shape, the OD decreasing as the platelet number (and hence TSP concentration) increases. However, the variation in OD obtained in the platelet concentration range associated with the normal population values, from 140 to 400×10⁹/L, is quite small for the antibody concentration chosen. This means that under the conditions used the test will be very sensitive in the region of abnormally low platelet count but fairly insensitive to variations in platelet numbers in the normal range.

Because it is necessary to run the calibration curve and the samples to be analyzed under the same conditions, all 26 normal donors were drawn the same morning and processed that afternoon and night. Hence, the calibration samples were run on the same plate and at the same time as the other 26 samples. It therefore was not possible to adjust the antibody concentration and re-run the set.

The low sensitivity over the normal range shown by the calibration curve is reflected in the results obtained on the 26 samples assayed. While the difference between the average value of the Counter (261×10⁹/L) and ELISA (300×10⁹/L) values (excluding sample 17 discussed below) was 15% of the Coulter mean, it is clear that the ELISA tended to be higher than the Coulter values. It is expected that this discrepancy will largely disappear with a more appropriate choice of antibody concentration.

However, part of the difference between the ELISA and Coulter results for normal donors may be significant. Sample 17 gave the biggest difference between the two measurements, the Counter giving 164×10⁹/L while the ELISA value was 324×10⁹/L. On examination of the light scattering distribution from the Coulter Counter it was found that this sample showed evidence of platelet aggregation, moving a significant fraction of the population out of the platelet counting window into he white cell window, resulting in a significant underestimate in the platelet count. Some of the other samples with large discrepancies may well have suffered from the same problem although only with sample 17 was the peak associated with platelet aggregates large enough to be flagged by the Coulter's software. Platelet counts are not identical from counter to counter and depend onto a certain degree on the setting of cutoffs to avoid counting other cell types, thus leading to underestimates if platelet aggregation is present. The ELISA, on the other hand, is not affected by platelet aggregation and gave a higher, and much more reliable value. This emphasizes that the immunoassay approach should provide more reliable platelet counts for abnormal, aggregated specimens which produce falsely low values in the Coulter Counter.

In a third study, blood samples from 10 patients with thrombocytopenia due to impaired platelet production were tested in the ELISA assay in parallel with samples from six normal donors. By Coulter analysis, the platelet counts in these patients ranged from 8×10⁹ to 78×10⁹ (where normal is >150×10⁹). The ELISA was carried out as described above, and a standard curve using purified thrombospondin was run on the same plate. Results are shown in FIG. 6, where open squares are donors with thrombocytopenia. FIG. 6 shows the relationship between the platelet count predicted by the thrombospondin inhibition ELISA and that of the Coulter STCKR for thrombocytopenic patients. As predicted from antibody binding studies described above, the thrombospondin ELISA was optimized to accurately estimate the platelet count when the platelet count is in the clinically abnormal range. Under these ELISA conditions, the accuracy of the count in abnormal samples is greater than that in samples where the platelet count is in the normal range. The correlation coefficient for the thrombospondin ELISA and the Coulter count in thrombocytopenic patients was 0.92.

EXAMPLE 4

Correlation Between Platelet Count and Concentration of β-thromboglobulin

Blood samples were collected from 32 donors with varying platelet counts, both within the normal range and below the normal range (thrombocytopenic samples). Two specimens were collected: one EDTA blood sample was used to determine the platelet count using a standard complete blood count instrument (Coulter STCKR), and one sample was used to generate a platelet-rich plasma sample. The sample used to generate the platelet-rich plasma sample was collected without any anticoagulant so that the clotting reaction would occur and the platelets would be activated to release the contents of their granules. The serum samples were used to determine the amount of the platelet granule protein, β-thromboglobulin, that was released from the platelets. This quantity was determined using an ELISA assay.

Figure 7:
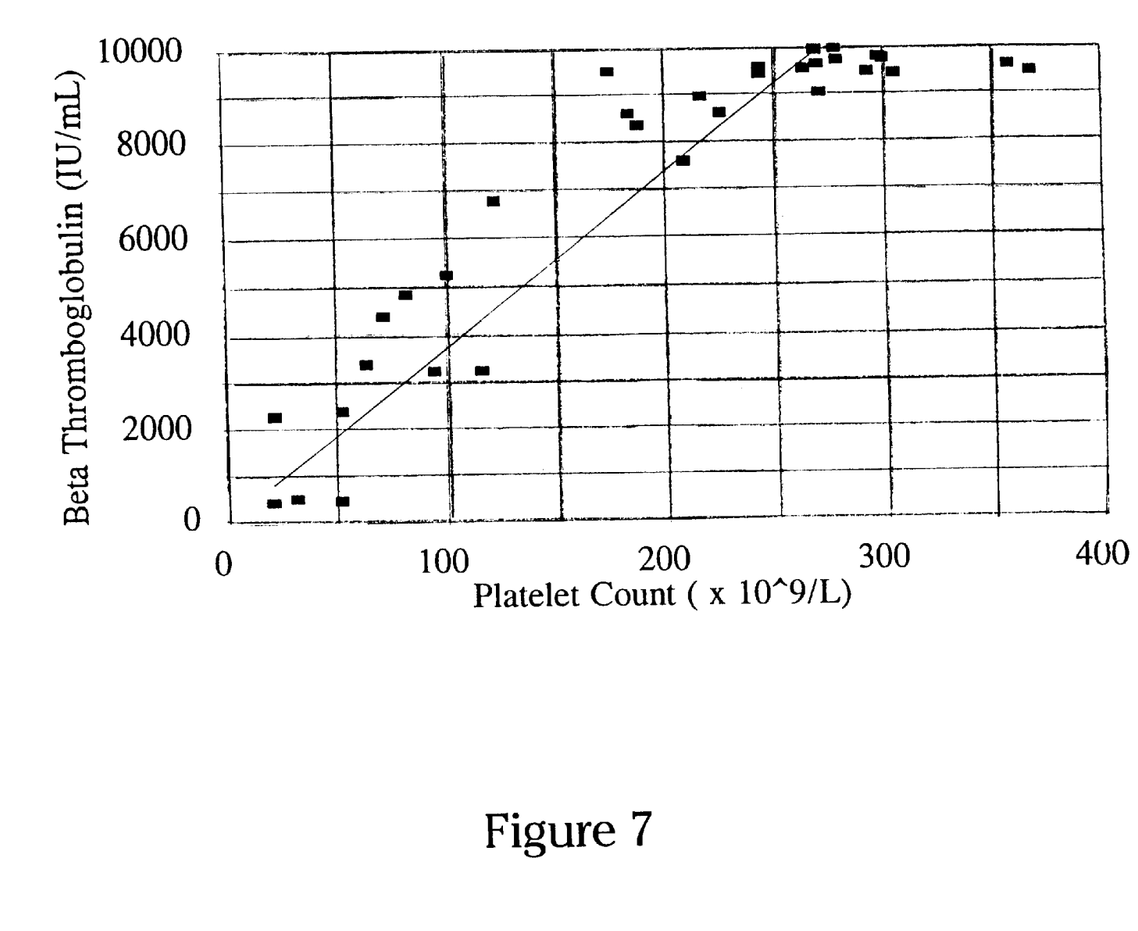
FIG. 7 is a graphic representation of the relationship between absolute platelet count as determined by the automated cell counter and the amount of the platelet granule protein, β-thromboglobulin, found in serum samples.

The results, reported in IU/ml, demonstrate that there is a strong positive correlation between the platelet count and the amount of β-thromboglobulin (FIG. 7; correlation coefficient =0.92). Thus, for the first time, Applicants have demonstrated a direct correlation between two different platelet granule proteins, thrombospondin and β-thromboglobulin, which is consistent both in normal donors and in donors with thrombocytopenia.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of determining platelet count of an individual, comprising the steps of:
   a) releasing platelet granule proteins from platelets in a blood sample from the individual, thereby generating a test sample comprising an amount of a released platelet granule protein of interest;
   b) measuring the amount of the released platelet granule protein of interest in the test sample, the released platelet granule protein of interest being selected from the group consisting of thrombospondin and β-thromboglobulin; and
   c) determining platelet count of the individual from the measured amount of the released platelet granule protein of interest in the test sample.

2. The method of claim 1, wherein the amount of the released platelet granule protein of interest is measured by an enzyme-linked immunosorbent assay.

3. The method of claim 1, wherein the amount of the released platelet granule protein of interest is measured by non-solid phase nephelometry.

4. The method of claim 1, wherein the platelet count is calculated from a standard curve.

5. A method of determining platelet count of an individual, comprising the steps of:
   a) isolating a platelet-rich plasma sample from a blood sample from the individual;
   b) releasing platelet granule proteins from platelets in the platelet-rich plasma sample, thereby generating a test sample comprising an amount of a released platelet granule protein of interest;
   c) measuring the amount of the released platelet granule protein of interest in the test sample, the released platelet granule protein of interest being selected from the group consisting of thrombospondin and β-thromboglobulin; and
   d) determining the platelet count of the individual from the measured amount of the released platelet granule protein of interest in the test sample.

6. The method of claim 5, wherein the amount of the released platelet granule protein of interest is measured by an enzyme-linked immunosorbent assay.

7. The method of claim 5, wherein the amount of the released platelet granule protein is measured by non-solid phase nephelometry.

8. The method of claim 5, wherein the platelet count is calculated from a standard curve.

* * * * *